US00PP10278P

United States Patent [19]

Murakami

[11] Patent Number: Plant 10,278

[45] Date of Patent: Mar. 10, 1998

[54] PETUNIA PLANT NAMED 'SUNBELKUHO'

[75] Inventor: Yasuyuki Murakami, Shiga, Japan

[73] Assignee: Suntory Limited, Osaka, Japan

[21] Appl. No.: 751,429

[22] Filed: Nov. 20, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,489 | 12/1993 | Hirabayashi et al. | Plt./68.1 |
| P.P. 8,768 | 6/1994 | Hirabayashi et al. | Plt./68.1 |
| P.P. 9,322 | 10/1995 | Tachibana et al. | Plt./68.1 |
| P.P. 9,341 | 10/1995 | Tachibana et al. | Plt./68.1 |
| P.P. 9,342 | 10/1995 | Sakazaki et al. | Plt./68.1 |
| P.P. 9,556 | 5/1996 | Tachibana et al. | Plt./68.1 |
| P.P. 9,557 | 5/1996 | Suzuki et al. | Plt./68.1 |
| P.P. 9,754 | 12/1996 | Suzuki et al. | Plt./68.1 |

*Primary Examiner*—James R. Feyrer
*Assistant Examiner*—Elizabeth C. Kemmerer
*Attorney, Agent, or Firm*—Burns, Doane, Swecker & Mathis, L.L.P.

[57] ABSTRACT

Disclosed herein is a petunia plant, having a decumbent habit plant having long stems. The petunia plant has over-abundant branching, particularly secondary branching strong, and great profusion blooms, the whole bush remaining in bloom for a considerable period of time. The flowers are single and very small, the petals having a white color, and the bottom color of the corolla throat and the outside color of corolla tube are light greenish yellow. The plant has a high resistance to rain, heat, drought and pest.

2 Drawing Sheets

BACKGROUND OF THE INVENTION

The present invention relates to a new and distinct variety of petunia plant obtained from the crossing of one petunia plant (♀), which was selected from a crossing a wild type of petunia plant called "A1" (♀) native to Brazil and the other wild type of petunia plant called "B1" (♂), and the wild type of petunia plant called "B1" (♂).

The petunia is a very popular plant and is used for flower bedding and potting in the summer season. There are only a few varieties of the petunia plant which do not have an upright growth habit and which have a high resistance to rain, cold, and diseases. The petunia which we previously filed, i.e., the "Revolution" series [(Revolution Purplepink (U.S. Plant Pat. No. 6,915), Revolution Brilliantpink (U.S. Plant Pat. No. 6,914), Revolution Brilliantpink-mini (U.S. Plant Pat. No. Plant 6,899)] is decumbent type plant having long stems, a lower plant height, abundant branching, and a high resistance to heat, cold and rain. However, there are only a few varieties having a great profusion of flowers, white color and very small flower and a high resistance to rain, heat, cold and diseases. Accordingly, this invention was aimed at obtaining a new variety having a white color and very small flower, together with the above features.

The new variety of petunia plant according to this invention originated from crossing one petunia plant (♀), which was selected from a crossing a wild type of petunia plant called "A1" (♀) native to Brazil and the other wild type of petunia plant called "B1" (♂), and the wild type of petunia plant called "B1" (♂).

First of all, 340 seedling were obtained from crossing a wild type of petunia plant called "A1" native to Brazil as female parent and the other wild type of petunia plant called "B1" as pollen parent in June, 1993. From this crossing 10 seedlings were selected in view of decumbent habit and flower color. And then 120 seedlings were obtained from a crossing of these selected 10 seedlings as female parent and the other wild type of petunia plant called "B1" as pollen parent in January, 1995. These 120 seedlings were grown and 10 seedlings were selected from these. These selected 10 seedlings were carried out a trial by flower potting and bedding, and then the only one plant selected in November, 1995. The botanically characteristics of the finally-selected plant were then examined, using similar variety "Pearl Sky Blue" for comparison, from May, 1995. As a result, it was concluded that this petunia is distinguishable from any other variety, whose existence is known to us, sufficiently uniform and stable in its characteristics, then this new variety of petunia plant was named "Sunbelkuho".

In the following description, the colour-coding is in accordance with the Horticultural Colour Chart of The Royal Horticultural Society, London, England (R.H.S. Colour Chart), and the Inter-Society colour Council-Nation Bureau of Standard Colour Name (I.S.C.C.-N.B.S. Colour Name). A colour chart based on The Japan Colour Standard for Horticultural Plant (J.H.S. Colour Chart) is also added for reference.

The female parent use in the crossing of "Sunbelkuho" was a wild type of petunia plant called "A1" (♂) native to Brazil, the seeds of which are gathered at Gramado, Rio Grande Do Sul, Brazil and introduced to Japan in December, 1989. The petunia plant "A1" having a decumbent habit plant having long stems, an over-abundant branching, great profusion blooms, flowers are single and small, the petals having a reddish purple color, leaf shape is elliptic, and a high resistance to rain, heat, drought and pest.

The pollen parent use in the crossing of "Sunbelkuho" was other wild type of petunia plant called "B1" (♂) native to Brazil, the seeds of which were gathered at Gramado, Rio Grande Do Sul, Brazil and introduced to Japan in December, 1992. The petunia plant "B1" having a decumbent habit plant having long stems, an over-abundant branching, great profusion blooms, flowers are single and small, the petals having a white color, leaf shape is lanceolate, and a high resistance to rain, heat, drought and pest. These wild type of petunia plants "A1" and "B1" are presently maintained at the Plant Biotechnology Laboratory of SUNTORY Ltd., residing at 863-1, Aza-Iketani, Oomori-cho, Youkaiti-shi, Shiga-ken, Japan.

The similar variety "Pearl Sky Blue" used for examination as a comparison are as follows.

Plant:
*Growth habit.*—Medium upright.
*Plant height.*—14 cm.
*Spreading area of plant.*—15–17 cm in diameter.
*Blooming period.*—April to September in the southern Kanto area, Japan.
Stem:
*Thickness.*—2.7 mm.
*Pubescence.*—Much.
*Branching.*—Abundant.
*Length of internode.*—1.3 cm.
Leaf:
*Shape.*—Elliptic.
*Length (average).*—5.5 cm.
*Width (average).*—3.5 cm.
*Color.*—Strong yellow green (R.H.S 144A, JHS 3507).
*Pubescence.*—Much.
*Thickness.*—0.5–0.6 mm.
*Leaf attaching angle to stem.*—Horizontal to droopy.
Flower:
*Facing direction.*—Upward.
*Type.*—Single.
*Shape.*—Funnel-shape, with five-fissured limb.
*Shape of petal tip.*—Obverse.
*Waving of petal.*—Week.
*Lobation of petal.*—Shallow.
*Diameter.*—5.5 cm.
*Color.*—Petal: Strong bluish purple (R.H.S. 83C, JHS 8310).
*Bottom color of the corolla throat and the outside color of corolla tube.*—Light yellow green (R.H.S. 3D, JHS 3304).
*Reproductive organs.*—1 normal pistil and 5 normal stamens
*Peduncle.*—0.7–0.9 mm in thickness, and 2.7 cm in length.
Physiological and ecological characteristics: Moderate resistance to heat, cold and disease and pest. Strong resistance to rain.

This new and distinct variety of petunia plant, "Sunbelkuho", was asexually reproduced by cutting at the aforementioned the Plant Biotechnology Laboratory of SUNTORY Ltd., and the homogeneity and stability thereof were confirmed.

SUMMARY OF THE VARIETY

The new variety of petunia plant has a decumbent habit, long stems and white flower petal and thus is very different from a similar variety, "Pearl Sky Blue". The plant has decumbent habit, over-abundant branching and great profusion blooms, and the whole bush remains in bloom for a considerable period of time. Especially secondary branching is strong. The flower are single and very small, which is clearly distinguished from small flower of "Pearl Sky Blue" and the petals having a white color, which is clearly distinguished from strong bluish purple of "Pearl Sky Blue". The bottom color of the corolla throat and the outside color of corolla tube are light greenish yellow. The plant has a high resistance to rain, heat, drought and pest.

DESCRIPTION OF THE VARIETY

Figure 1:
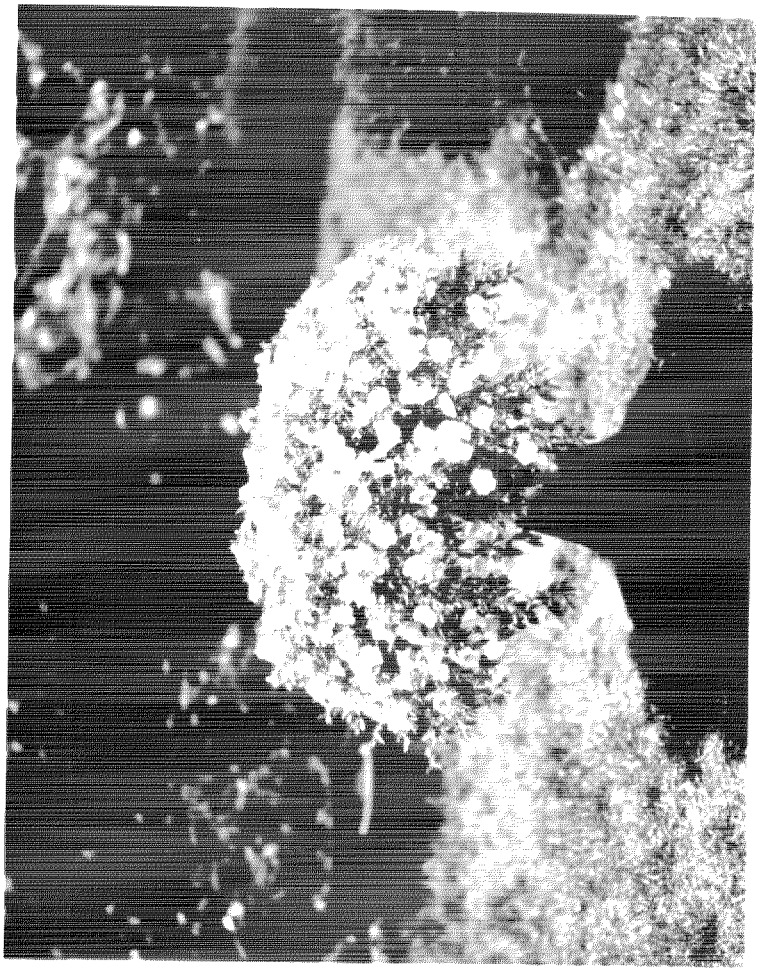
FIG. 1 is a photograph giving a partial view of the new variety of petunia plant planted in a flower pot.
Figure 2:
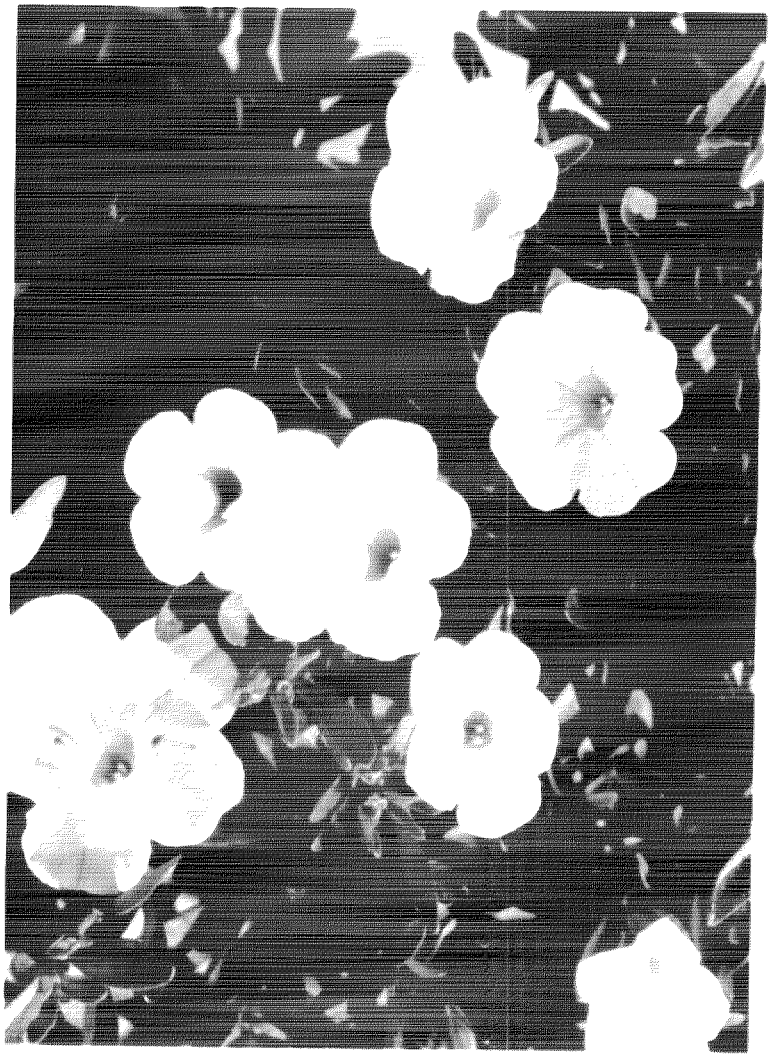
FIG. 2 is a photograph of flowers of the new variety of petunia plant.

The botanical characteristics of the new and distinct variety of petunia plant "Sunbelkuho" are as follows.

Plant:
*Growth habit.*—Decumbent. The stems hang down when potted in a hanging pot.
*Plant height.*—6–7 cm.
*Spreading area of plant.*—The stem extends to length of 20–25 cm from the base, and thus the spreading area of the plant is 80 cm in diameter.
*Growth.*—Very vigorous with abundant branching, a great profusion of blooms; the whole bush remaining in bloom for a considerable this period of time.
*Blooming period.*—May to late October in the southern Kanto area, Japan. The plant shape does not change throughout this period.
Stem:
*Thickness.*—1.2 mm.
*Pubescence.*—Normal.
*Branching.*—Over-abundant. Particularly secondary branching is very strong.
*Length of internode.*—1.2 cm.
Leaf:
*Shape.*—Lanceolate.
*Length.*—3.5 cm.
*Width.*—1.1 cm.
*Color.*—Deep yellow green. (R.H.S. 146A, JHS 3508)
*Thickness.*—0.4 mm.
*Pubescence.*—Few.
*Leaf attaching angle to stem.*—Slantly upward to horizontal.
Flower:
*Facing direction.*—Slantly upward to horizontal.
*Type.*—Single.
*Shape.*—Funnel-shape, with five-fissured limb.
*Shape of petal tip.*—Medium.
*Waving of petal.*—Week.
*Lobation of petal.*—Shallow.
*Diameter.*—2.6–2.8 cm.
*Color.*—Petal: White (R.H.S. 155A, JHS 01).
*Bottom color of the corolla throat and the outside color of corolla tube.*—Light greenish yellow (R.H.S. 2A, JHS 2904).
*Reproductive organs.*—1 normal pistil and 5 normal stamens. Both normal.
*Peduncle.*—0.6–0.8 mm in thickness, and 1.6 cm in length.
Physiological and ecological characteristics: High resistance to rain, heat, drought and pest, especially resistance to rain and heat is very strong.

This new variety of petunia plant is most suitable for flower bedding and potting, particularly in hanging pots or planters, and further excellent for ground cover.

The plant of this new variety "Sunbelkuho" is presently planted and maintained at the Plant Biotechnology Laboratory of SUNTORY Ltd., residing at 863-1, Aza-Iketani, Oomori-cho, Youkaiti-shi, Shiga-ken, Japan.

I claim:

1. A new and distinct variety of petunia plant, substantially as herein illustrated and described, characterized particularly as to novelty by (A) being a decumbent habit plant having long stems, (B) an over-abundant branching, particularly secondary branching is strong, and great profusion blooms, the whole bush remaining in bloom for a considerable period of time, (C) flowers are single and very small, the petals having a white color, and the bottom color of the corolla throat and the outside color of corolla tube are light greenish yellow (D) a high resistance to rain, heat, drought and pest.

* * * * *

SUNBELKUHO

SUNBELKUHO